US011254988B2

(12) United States Patent
Yan et al.

(10) Patent No.: US 11,254,988 B2
(45) Date of Patent: Feb. 22, 2022

(54) SOMATIC MUTATIONS IN ATRX IN BRAIN CANCER

(71) Applicants: The Johns Hopkins University, Baltimore, MD (US); Duke University, Durham, NC (US)

(72) Inventors: Hai Yan, Chapel Hill, NC (US); Darell Bigner, Mebane, NC (US); Bert Vogelstein, Baltimore, MD (US); Kenneth W. Kinzler, Baltimore, MD (US); Alan Meeker, Pikesville, MD (US); Ralph Hruban, Baltimore, MD (US); Nickolas Papadopoulos, Towson, MD (US); Luis Diaz, Ellicot City, MD (US); Yuchen Jiao, Baltimore, MD (US)

(73) Assignees: The Johns Hopkins University, Baltimore, MD (US); Duke University, Durham, NC (US)

( * ) Notice: Subject to any disclaimer, the term of this patent is extended or adjusted under 35 U.S.C. 154(b) by 197 days.

(21) Appl. No.: 15/989,820

(22) Filed: May 25, 2018

(65) Prior Publication Data
US 2018/0334726 A1  Nov. 22, 2018

Related U.S. Application Data

(62) Division of application No. 14/129,850, filed as application No. PCT/US2012/044631 on Jun. 28, 2012, now Pat. No. 9,982,306.

(60) Provisional application No. 61/502,646, filed on Jun. 29, 2011.

(51) Int. Cl.
G01N 33/574 (2006.01)
C12Q 1/6886 (2018.01)
C07K 16/40 (2006.01)
C12N 15/113 (2010.01)

(52) U.S. Cl.
CPC .......... C12Q 1/6886 (2013.01); C07K 16/40 (2013.01); C12N 15/1137 (2013.01); G01N 33/57407 (2013.01); *C12Q 2600/118* (2013.01); *C12Q 2600/156* (2013.01)

(58) Field of Classification Search
CPC  C12Q 1/6886; C12Q 2600/118; C07K 16/40; C12N 15/1137; G01N 33/57407
See application file for complete search history.

(56) References Cited

U.S. PATENT DOCUMENTS

| 2002/0110820 A1 | 8/2002 | Ramaswamy et al. |
| 2004/0005642 A1 | 1/2004 | Liau |
| 2007/0009927 A1* | 1/2007 | Cho ............... C12Q 1/6883 435/6.16 |

FOREIGN PATENT DOCUMENTS

| WO | 2008021483 | 2/2008 |
| WO | 2008132752 | 11/2008 |

OTHER PUBLICATIONS

Jiao et al, Science 331:1199-1203, online published Apr. 28, 2011, IDS #31 filed on Dec. 3, 2018 (Year: 2011).*
Azzalin et al., "Telomeric Repeat—Containing NA and RNA Surveillance Factors at Mammalian Chromosome Ends," Science 318, 798 (Nov. 2, 2007).
Bello et al., "High-Resolution analysis of Chromosome Arm 1p alterations in Meningioma," Cancer Genetics and Cytogenetics, vol. 120, Jan. 1, 2000, pp. 30-36.
Bello et al., "hRAD54 Gene and 1p High-Resolution Deletion-Mapping Analyses in Oligodenrogliomas," Cancer Genetics and Cytogenetics, vol. 116, No. 1, Jan. 1, 2000, pp. 142-147.
Blackburn, "Structure and Function of Telomeres," Nature 350, 569 (Apr. 18, 1991).
Bryan et al., "Evidence for an alternative mechanism for maintaining telemore length in human tumors and tumor-derived cell lines," Nat Med 3, 1271 (Nov. 1997).
Cerone et al., "A human cell line that maintains telomeres in the absence of telomerase and of key markers of ALT," Oncogene 24, 7893 (Nov. 24, 2005).
Cesare et al., "Alternative lengthening of telomeres: models, mechanisms, and implications," Nat Rev Genet 11, 319 (May 2010).
Chen et al., "Single base discrimination of CENP-B repeats on mouse and human Chromosomes with PNA-FISH," Mamm Genome 10, 13 (Jan. 1999).
Elsaesser et al., "DAXX is an H3.3-specific histone chaperone and cooperates with ATRX in replication-independent chromatin assembly at telomeres," Proc Natl Acad Sci USA 107, 14075 (Aug. 10, 2010).
Extended European Search Report issued in related European Application No. 12804757.8, dated Feb. 11, 2015.
Fasching et al., "Telomerase_Independent Telomere Length Maintenance in the Absence of Alternative Lengthening of . . . "Cancer Res 65, 2722 (Apr. 1, 2005).
Garcia-Cao, Nat Genet 36, "Epigenetic regulation of telomere length in mammalian cells by the Suv39hl and Suv39H2 histone methltransferases," 94 (Jan. 2004 ).

(Continued)

*Primary Examiner* — Lei Yao
(74) *Attorney, Agent, or Firm* — Fish & Richardson P.C.

(57) ABSTRACT

We determined the sequence of ATRX and DAXX in 447 cancers from various sites. We found mutations most commonly in pediatric glioblastoma multiformae (GBM) (11.1%), adult GBM (6.5%), oligodendrogliomas (7.7%) and medulloblastomas (1.5%); and showed that Alternative Lengthening of Telomeres (ALT), a telomerase-independent telomere maintenance mechanism found in cancers that have not activated telomerase, perfectly correlated with somatic mutations of either gene. In contrast, neuroblastomas, and adenocarcinomas of the ovary, breast, and pancreas were negative for mutations in ATRX and DAXX. Alterations in ATRX or DAXX define a specific molecular pathway that is closely associated with an alternative telomere maintenance function in human cancers.

7 Claims, 3 Drawing Sheets
Specification includes a Sequence Listing.

(56) References Cited

OTHER PUBLICATIONS

Gibbons et al., "Mutationd in the Chromatin-Associated Protein ATRX," Hwn Mutat 29, 796 (Jun. 2008).
Gibbons et al., "Mutations in a putative global transcriptional regulator cause X-linked mental retardation with a-thalasssemia (ATR-X syndrome," Cell 80, 837 Mar. 24, 1995).
Gibbons et al., "Mutations in ATRX, encoding a SWI/SNF-like protein, cause diverse changes in the pattern of DNA methylation," Nat Genet 24, 368 (Apr. 2000).
Gibbons, "Alpha Thalassaemia-mental retardation, X linked," Orphanet J Rare Dis 1, 15 (2006).
Goldberg et al., "Distinct Factors Control Histone Variant H3.3 Localization at Specific Genomic Regions," Cell 140, 678-691 (Mar. 5).
Gonzalo et al., "DNA Methyltransferases control telomere length and telomere recombination in mammalian cells," Nat Cell Biol 8, 416 (Apr. 2006).
Grafi et al., "Histone Methylation Telomerase-independent telomere lengthening in cells undergoing dedifferentiation," Dev Biol 306, 838 (Jun. 15, 2007).
Heaphy, C. M. et al., Altered Telomeres in Tumors with ATRX and DAXX Mutations.,Science, vol. 333, pp. 425, Jul. 22, 2011.
Henson et al., "A Robust Assay for Alternative Lengthening of Telomeres in Tumors Shows the Significance of Alternative Lengthening of Telomeres in Sarcomas and Astrocytomas," Clinical Cancer Research, Jan. 1, 2005, p. 217.
Henson et al., "Assaying and investigating Alternative Lengthening of Telomeres activity in human cells and cancers," FEBS Lett 584, 3800 (Sep. 10, 2010).
International Search Report dated Jan. 29, 2013, for PCT/US2012/044631.
Jeuken et al., "Molecular pathogenesis of oligodendroglial tumors," Journal of Neuro-Oncology, vol. 70, No. 2, Nov. 1, 2004, pp. 161-181.
Jiao et al, Oncotarget, 3:709-722, 2012.
Jiao et al, Science 331 :1199-1203, on line published Apr. 28, 2011.
Law et al., "ATR-X Syndrome Protein Targets Tandem Repeats and Influences Allele-Specific Expression in a Size-Dependent Manner," Cell 143, 367 (Oct. 29).
Levy et al., "Telomere end-replication problem and cell aging," J Mol Biol 225, 951 (Jun. 20, 1992).
Makarov et al., "Nucleosomal Organization of Telomere-Specific Chromatin in Rat," Cell 73, 775 (May 21, 1993).
Marciniak et al., "A Novel Telomere Structure in a Human Alternative Lengthening of Telomeres Cell Line," Cancer Res 65, 2730 (Apr. 1, 2005).
Meeker at al., "Telomerase: a Promising Marker of Biological Immortalitu of Germ, Stem, and Cancer Cells. A Review," Biochemistry (Mose) 62, 1323 (Nov. 1997).
Meeker et al., "Telomere Length Assessment in Human Archival Tissues," Arn J Pathol 160, 1259 (Apr. 2002).
Montgomery et al., "Telomere Lengths of Translocation-Associated and Nontranslocation-Associated Sarcomas Differ Dramatically," Am J Pathol 164, 1523 (May 2004).
Mukasa et al., "Distinction in Gene Expression Profiles of Oligodendrogliomas With and Without Allelic Loss of 1 P," Oncogene, vol. 21, No. 25, Jun. 6, 2002, pp. 3961-3967.
Muntoni et al., "Telomere elongation involves intra-molecular DNA replication in cells utilizing alternative lengthening of telomeres," Hum Mol Genet 18, 1017 (Mar. 15, 2009).
Olovnikov,"A Theory of Marginotomy the Incomplete Copying of Template Margin in Enzymic Synthesis of Polynucleotides and Biological Signifigance of the Phenomenon," J Theor Biol 41, 181(Sep. 14, 1973).
Reddel et al., "Alternative Lengthening of Telomeres in Human Cells," Radiat Res 155, 194 (Jan. 2001).
Shay et al., "A Survey of Telomerase Activity in Human Cancer," Eur J Cancer 33, 787 (Apr. 1997).
Shih et al., "Daxx Mediates SUMO-dependent transcriptional control and subnuclear compartmentalization," Biochern Soc Trans 35, 1397 (Dec. 2007).
Subhawong et al., "1688 Alternative Lengthening of Telomeres in Human Carcinoma Subtypes," (2011).
Tanori et al., "Opposite modifying effects of HR and NHEJ deficiency on cancer risk in Ptc 1 heterozygous mouse cerebellum," Oncogene, vol. 30, No. 47, May 23, 2011, pp. 4740-4749.
Wong et al., "ATRX interacts with H3.3 in maintaining telomere structural integrity in pluripotent embryonic stem cells," Genome Res 20, 351 (Mar.).
Wong et al., "Histone H3.3 incorporation provides a unique and functionally essential telomeric chromatin in embryonic stem cells," Genome Res 19, 404 (Mar. 2009).
Xue et al., "The ATRX syndrome protein forms a chromatin-remodeling complex with Daxx and localizes in promyelocytic leukemia nuclear bodies," Proc Natl Acad Sci US A 100, 10635 (Sep. 16, 2003).
Y. Jiao et al., "DAXX/ATRX, MEN1 and mTOR Pathway Genes are Frequently Altered in Pancreatic Nueroendocrine Tumors," *Science*, Mar. 4, 2011, (6021):1199-1203.
Yeager et al., "Telomerase-negative Immortalized Human Cells Contain a Novel Type of Promyelocytic Leukemia (PML) Body,"Cancer Res 59, 4175 (Sep. 1, 1999).
Bisoffi et al., "Telomeres: Prognostic markers for solid tumors," International Journal of Cancer, 2006, 117(10):2255-2260 DOI: 10.1002/ijc.22120.
Elsaesser et al., "HIRA and Daxx Constitute Two Independent Histone H3.3-Containing Predeposition Complexes," Cold Spring Harb Symp Quant Biol., 2010, LXXV:27-34.
Henson et al., "Alternative lengthening of telomeres in mammalian cells," Oncogene, 2002, 21:598-610.
PCT International Preliminary Report on Patentability in International Appln. No. PCT/US2012/044631, dated Jan. 16, 2014, 6 pages.

* cited by examiner

SOMATIC MUTATIONS IN ATRX IN BRAIN CANCER

This application is a divisional of U.S. application Ser. No. 14/129,850, filed Apr. 7, 2014, which is a national stage application, filed under 35 U.S.C. § 371 of International Application No. PCT/US2012/044631, filed Jun. 28, 2012, which claims priority to and the benefit of U.S. Provisional Patent Application No. 61/502,646, filed Jun. 29, 2011; the contents of which are hereby incorporated by reference in their entireties.

This invention was made with government support under grants CA043460, CA057345, CA140316, and CA206423 awarded by the National Institutes of Health. The government has certain rights in the invention.

TECHNICAL FIELD OF THE INVENTION

This invention is related to the area of cancer. In particular, it relates to brain cancers.

BACKGROUND OF THE INVENTION

Telomeric DNA functions to stabilize chromosomal ends and is progressively lost during cell division (the end replication problem), thus limiting cellular proliferative capacity.(1-3) The majority of cancers solve the end replication problem by expressing the telomere-synthesizing enzyme telomerase. A subset of the others utilizes a genetic recombination-based telomerase-independent telomere maintenance mechanism termed alternative lengthening of telomeres (ALT).(4-7) The prevalence of ALT varies widely, but is found more often in cancers of the central nervous system (CNS) and of mesenchymal tissues than in common epithelial tumors.(8, 9)

A recent study of pancreatic neuroendocrine tumors (PanNETs) revealed that 43% harbored inactivating mutations in the ATRX or DAXX genes.(10) Notably, these mutations were mutually exclusive, indicating that they functioned in the same pathway. This mutual exclusivity was intriguing, as independent studies had shown that the proteins encoded by ATRX and DAXX interact with one another.(11) The ATRX gene encodes a large protein possessing a C-terminal helicase/ATPase domain placing it in the SNF2 family of chromatin remodeling enzymes.(12) Inherited mutations in ATRX cause X-linked alpha thalassemia/mental retardation syndrome, characterized by multiple developmental abnormalities in affected males.(13, 14) DAXX is a nuclear protein that interacts with numerous SUMO-modified proteins and plays a role in transcriptional repression.(15) The ATRX and DAXX protein complex has been suggested to play multiple cellular roles, including functioning in chromatin remodeling.(11, 16) Notably, the ATRX/DAXX complex was recently found to be required for the incorporation of the histone variant H3.3 at telomeres.(17-19) This histone chaperone activity may play a role in establishing or maintaining telomere stability, at least in mouse embryonic stem cells.(20, 21) Reducing either ATRX or H3.3 levels in these cells decreased the amount of heterochromatic protein HP1-alpha at telomeres and increased markers of telomere dysfunction.(20, 21) Epigenetic changes in telomeric and subtelomeric chromatin have also been shown to affect telomere length, as well as recombination at telomeres. (22-24)

There is a continuing need in the art to identify markers for diagnosis, prognosis, stratifying, and targeting of brain tumors.

SUMMARY OF THE INVENTION

According to one aspect of the invention a method predicts outcome of a central nervous system (CNS) tumor in a patient. The CNS tumor is tested, or cells or nucleic acids shed from the tumor are tested, for the presence of an inactivating mutation in ATRX. The mutation is a positive prognostic indicator.

According to another aspect of the invention a method identifies a CNS tumor. The presence of an inactivating mutation in ATRX is tested for and identified in a tissue suspected of being a CNS tumor, or in cells or nucleic acids shed from the tumor. The presence of an inactivating mutation indicates a CNS tumor.

According to still another aspect, a method inhibits ATRX in a CNS tumor. An ATRX inhibitory agent is administered to the CNS tumor. The agent inhibits ATRX function or expression.

These and other embodiments which will be apparent to those of skill in the art upon reading the specification provide the art with methods for assessing, identifying, diagnosing, prognosticating, stratifying, and treating tumors of the central nervous system.

BRIEF DESCRIPTION OF THE DRAWINGS

(FIG. 1A) ALT-negative PanNET. Telomere FISH signals are markedly dimmer in PanNET cells (*) than in the surrounding stromal cells (arrowheads). Centromere-specific FISH probe serves as positive control for hybridization. (FIG. 1B and FIG. 1C) Immunolabeling of same PanNET as in A, shows nuclear positivity for ATRX and DAXX proteins, respectively. (FIG. 1D) Example of ALT-positive PanNET. Large, ultra-bright telomere FISH signals indicative of ALT are indicated (arrows). (FIG. 1E) Immunolabeling of same PanNET as in D, shows loss of nuclear DAXX protein in tumor cells. Benign endothelial cells (arrowheads) serve as positive staining controls. (FIG. 1F and FIG. 1G) Examples of ALT-positive GBM and medulloblastoma, respectively. Original magnification=400× for all images.

(FIG. 2A) ALT-positive PanNET telomere FISH and ATRX protein. (FIG. 2B) same image as in A, omitting telomere and DAPI channels, highlighting loss of nuclear ATRX. Benign stromal cells positive for nuclear ATRX protein are indicated by arrows. (FIG. 2C) ALT-positive PanNET co-stained with telomere FISH and DAXX protein. (FIG. 2D) same image as in FIG. 2C, omitting telomere and DAPI channels. Punctate nuclear DAXX staining in benign stromal cells is indicated by arrow heads. E, ALT-positive medulloblastoma stained for telomere FISH and PML protein. Arrows show co-localization of PML protein and ALT-associated telomere foci. F&G, high magnification images of telomere and PML protein co-staining showing typical targetoid appearance of ALT-associated PLM bodies (APB). Original magnification=400× for images FIG. 2A-FIG. 2AE, 1000× for images FIG. 2F and FIG. 2G.

(FIG. 3A) ALT-positive osteosarcoma cell line U2-OS showing lack of nuclear ATRX protein. (FIG. 3B) ALT-negative PanNET cell line BON-1 showing ATRX nuclear-positivity. In both cases the nuclear DNA was counter stained with DAPI. Original magnification=400×.

DETAILED DESCRIPTION OF THE INVENTION

Figures 1A, 1B, 1C, 1D, 1E, 1F, 1G:
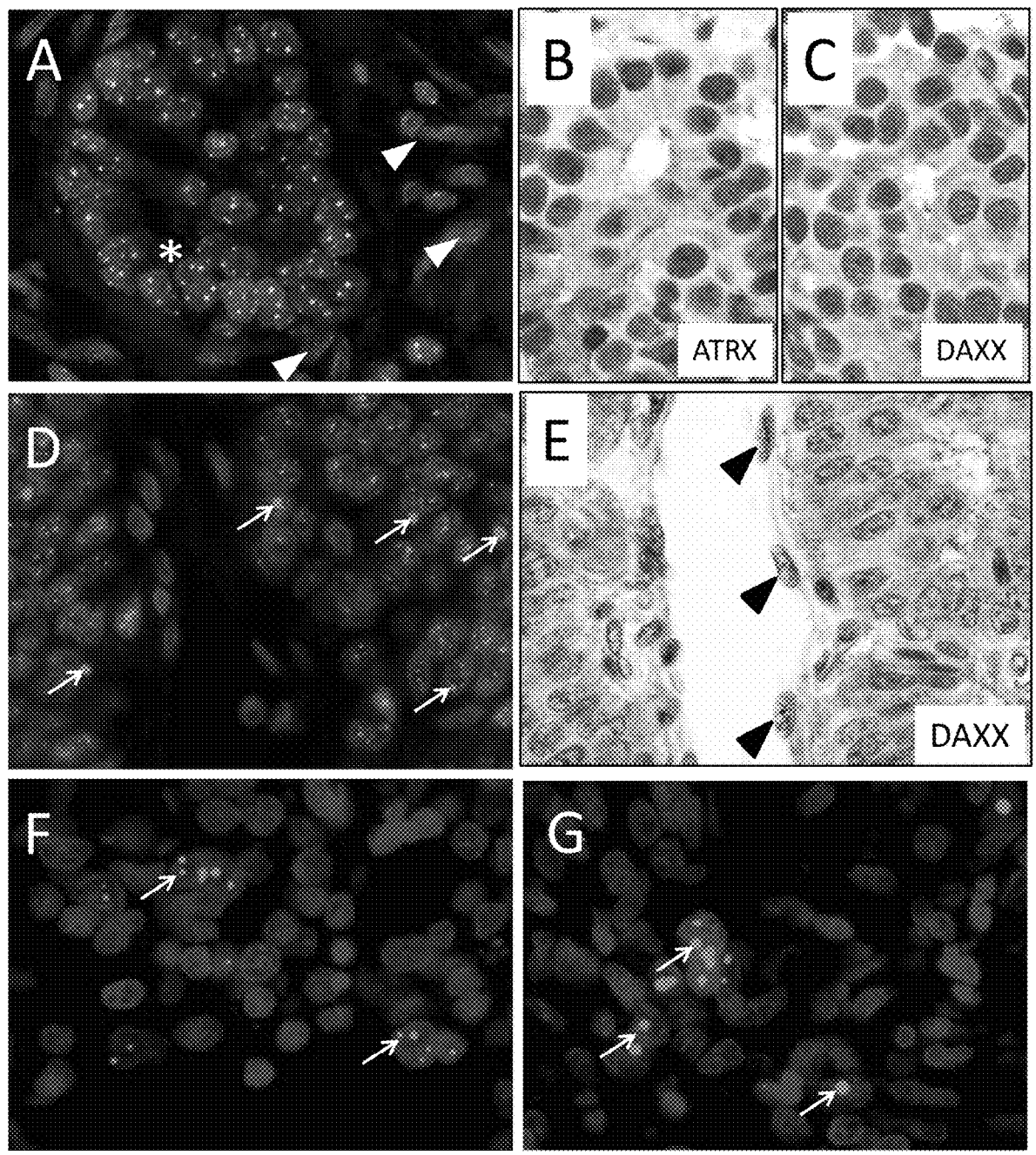
FIG. 1A-1G. Representative images of ALT-negative and ALT-positive tumors.

The inventors have found that ATRX mutations are frequently found in tumors of the central nervous system. Moreover, they are mutated together with IDH1 or IDH2 and TP53. ATRX mutations appear to be a later event in the progression of the brain tumors than the other mutations. Thus somatic mutations in ATRX can be used as a diagnostic, prognostic, or stratifying factor for such tumors.

Tumors of the CNS which may be assessed and treated include without limitation medullobalstoma, oligodendroglioma, pediatric glioblastoma multiforme, adult glioblastoma multiforme, oligoglioma, anaplastic oligodendroglioma, oligoastroglioma, anaplastic oligoastrocytoma, astrocytoma, anaplastic astrocytoma, ependymoma, anaplastic ependymoma, myxopapillary ependymoma, subependymoma, mixed glomas, polar spongioblastomas, astroblastoma, gliomatosis cerebri, medulloepithelioma, neuroblastoma, retinoblastoma, and ependymoblastoma. Glial tumors of any type may be assessed and treated.

Tests for ATRX mutations can be performed using protein based or nucleic based assays. Sequence determination of the nucleic acid can be used to identify mutations. Probes or primers, and kits and techniques employing both can be used. PCR or other specific or global amplification can be used. Mutations can be identified in any available genetic material including or example genomic DNA, cDNA, and RNA. Nucleic acids can be amplified, enriched, and/or purified prior to assessment. Protein based assays may involve specific antibodies and/or ATRX binding partner DAXX. The antibodies may be polyclonal or monoclonal, fragments (Fab, Fab'), single chain constructs (scFv), etc. Nucleic acid based assays include without limitation, hybridization to probes, amplification using specific primers, primer extension, ligation assay, etc. Any of these techniques can also be combined. Assays can be performed together with tests for other gene mutations or alterations of the genome. Results can be integrated and used to accurately and comprehensively characterize and/or identify a tumor or the patient.

Results of assays can be recorded in a written medium, an electronic medium, or transmitted orally or electronically to a health care provider, a patient, a family member, a hospital, etc. Testing requires physical steps, and typically involves chemical changes to occur to a test sample. Typically the test sample is a sample that is removed from the patient body, so that the test is performed outside of a patient body.

Samples which may be tested include without limitation brain tissue, tumor tissue, CNS fluid, neuronal tissue, blood, urine, saliva, tears, sputum, etc. These samples may be collected and processed and/or stored prior to testing. The samples may be frozen or fixed. They may be archival or freshly collected. Typically the tissue or body fluid will be isolated from the body and the assay will be performed ex vivo on the isolated sample.

ATRX inhibitory agents as used in this specification inhibit either ATRX function or expression. Such agents may be an antibody, an antibody fragment, or a single chain antibody construct. Alternatively it can be an inhibitory RNA or other inhibitory nucleic acid molecule, including but not limited to antisense oligonucleotides, antisense expression constructs, siRNA, and RNAi.

Any type of mutation may be identified. Inactivating mutations include without limitation R2079X, Q1874X, Q1788H, E2277K, Q2156H, K455X, W263X, R2153C, and R1803H. The mutation may be, for example, a frameshift mutation, a splice-site mutation, an indel (insertion or deletion) mutation, a large genomic rearrangement, or a missense mutation. Typically an indel may involve a small portion of a gene, such as 1-10 nt. A large rearrangement may involve large portions or all of a gene, such as greater than 10%, greater than 25%, greater than 50%, greater than 75% or greater than 100% of a gene. Particular mutations which may be identified include g.chrX:76778161_76778162insA; g.chrX:76824745_76824748delTCTC; g.chrX:76741670_76741673delCTAT; g.chrX:76798738_76798741delACTA; g.chrX:76665385C>A; g.chrX:76825188_76825194delTTGAGGA; g.chrX:76831065delG(hom); g.chrX:76806828_76806829insT; g.chrX:76825743_76825744delTG; g.chrX:76798774_76798775delAG(hom); g.chrX:76826615C>T (hom); g.chrX:76700843G>A(hom); and g.chrX:76760970C>T.

Stratification of patients can be used to assign a treatment regimen. It may be used in prospective or retrospective clinical studies. It can be used to assign a prognosis. Stratification typically assigns a patient to a group based on a shared mutation pattern or other observed characteristic or set of characteristics.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

Example 1

ATRX and DAXX Gene Mutations Correlate with ALT-positivity

Given the potential role of ATRX and DAXX in modulating telomeric chromatin, we evaluated telomere status in pancreatic neuroendocrine tumors (PanNETs) with known ATRX and DAXX mutational status. Telomere-specific fluorescence in situ hybridization (FISH) was used to directly assess the telomeres in PanNETs. Neoplasms with ALT are readily distinguishable by large ultra-bright telomere FISH signals—a nearly universal feature of ALT-positive cell populations. (25) Although telomere FISH signals from these individual bright foci have often been shown to co-localize with PML protein, this localization is not as reliable as the strength of the FISH signals and was not used for classification in our study.(26-28)

Twenty-five of the 41 PanNETs (61%) examined by telomere FISH displayed evidence of ALT (Table 1, FIG. 1). Importantly, ALT was not observed in any of the surrounding non-neoplastic cells, including stromal fibroblasts, pancreatic acini, pancreatic ducts and islets of Langerhans (FIGS. 1 & 2).(29) ATRX and DAXX gene mutations both were significantly correlated with ALT-positivity (p<0.008 for either gene). In particular, all 21 (100%) PanNETs with ATRX or DAXX gene mutations were ALT-positive by telomere FISH (Table 1).

TABLE 1

PanNET cases grouped according to mutation status for ATRX and DAXX
and displaying ALT-status and immunohistochemistry of ATRX and DAXX

| Gene Status | Case | ALT-status* | ATRX IHC† | DAXX IHC† |
|---|---|---|---|---|
| ATRX Point mutations & indels | PanNET5 | Pos | Neg | Pos |
| | PanNET13 | Pos | Neg | Pos |
| | PanNET27 | Pos | Neg | Pos |
| | PanNET35 | Pos | Neg | Pos |
| | PanNET52 | Pos | Neg | Pos |
| | PanNET59 | Pos | Pos | Pos |
| | PanNET61 | Pos | Neg | Pos |
| | PanNET78 | Pos | Pos | Pos |
| | PanNET85 | Pos | Neg | Pos |
| | PanNET112‡ | Pos | Neg | Pos |
| DAXX Point mutations & indels | PanNET25 | Pos | Pos | Het |
| | PanNET31 | Pos | Pos | Het |
| | PanNET44 | Pos | Pos | Neg |
| | PanNET56 | Pos | Pos | Neg |
| | PanNET77 | Pos | Pos | Neg |
| | PanNET80 | Pos | Pos | Neg |
| | PanNET84 | Pos | Pos | Het |
| | PanNET87 | Pos | Pos | Het |
| | PanNET93 | Pos | Pos | Neg |
| | PanNET104 | Pos | Pos | Neg |
| | PanNET133 | Pos | Pos | Neg |
| ATRX/DAXX WT for Point mutations & indels | PanNET6 | Neg | Pos | Pos |
| | PanNET10 | Neg | Pos | Pos |
| | PanNET21 | Neg | Pos | Pos |
| | PanNET24 | Neg | Pos | Pos |
| | PanNET29 | Pos | Pos | Het |
| | PanNET36 | Neg | Pos | Pos |
| | PanNET39 | Pos | Neg | Pos |
| | PanNET45 | Pos | Pos | Neg |
| | PanNET57 | Neg | Pos | Pos |
| | PanNET63 | Neg | Pos | Pos |
| | PanNET64 | Pos | Het | Pos |
| | PanNET66 | Neg | Pos | Pos |
| | PanNET69 | Neg | Pos | Pos |
| | PanNET79 | Neg | Pos | Pos |
| | PanNET83 | Neg | Pos | Pos |
| | PanNET91 | Neg | Pos | Pos |
| | PanNET121 | Neg | Pos | Pos |
| | PanNET126 | Neg | Pos | Pos |
| | PanNET128 | Neg | Pos | Pos |
| | PanNET129 | Neg | Pos | Pos |

*The intensity of telomere FISH signals was assessed to be either negative or positive for the ALT phenotype.
†Immunohistochemistry was scored as uniformly positive, negative or heterogeneous for nuclear labeling.
‡Multifocal tumor, featuring ALT and negative nuclear immunolabeling in the majority of the tumor.
ALT, alternative lengthening of telomeres; Het, heterogeneous; IHC, immunohistochemistry; Neg, negative; PanNET, pancreatic neuroendocrine tumor; Pos, positive; WT, wild type.

Figures 2A, 2B, 2C, 2D, 2E, 2F, 2G:
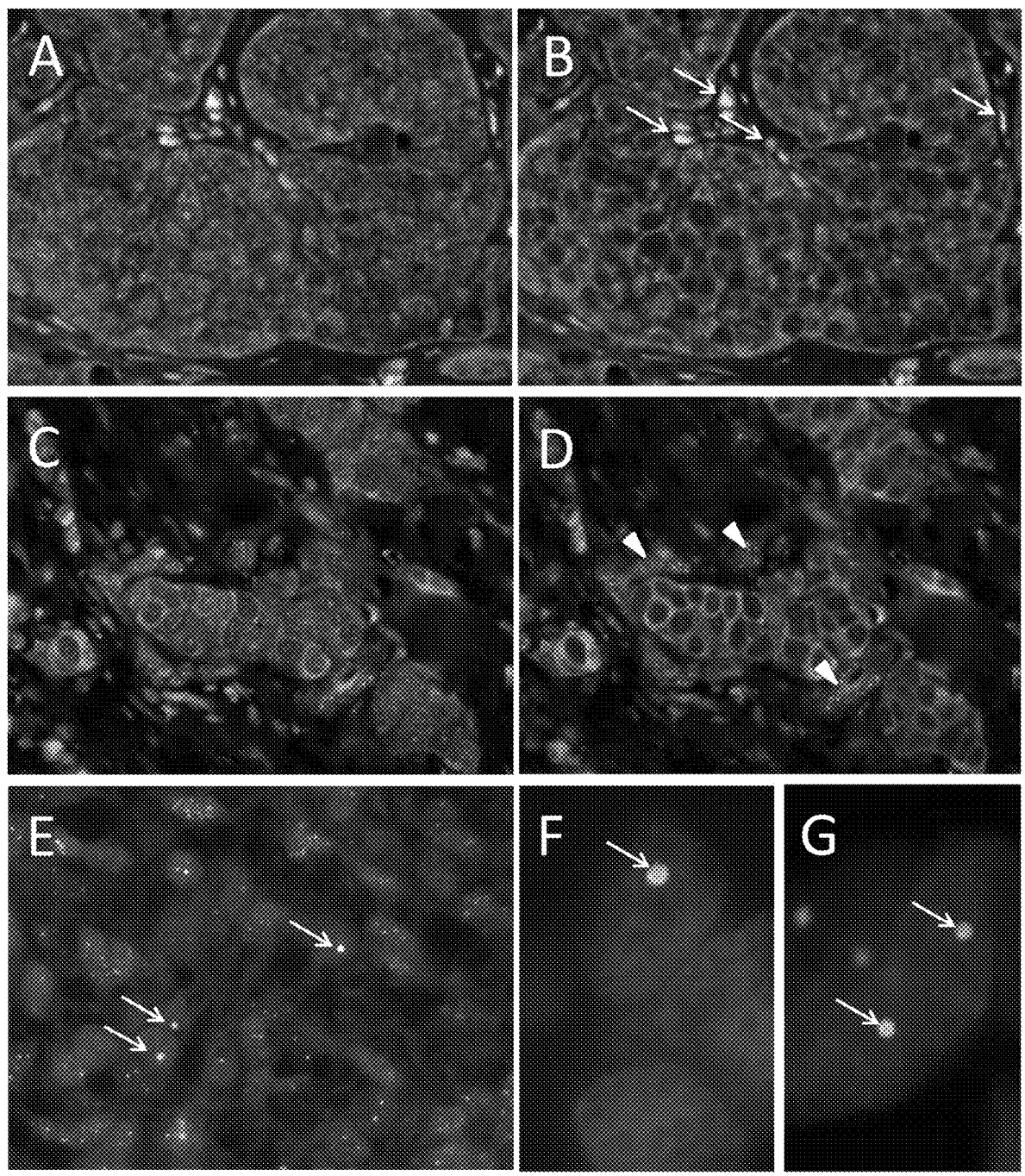
FIG. 2A-2G. Telomere-FISH and immunofluorescence co-staining in ALT-positive tumors.
Figure 3:
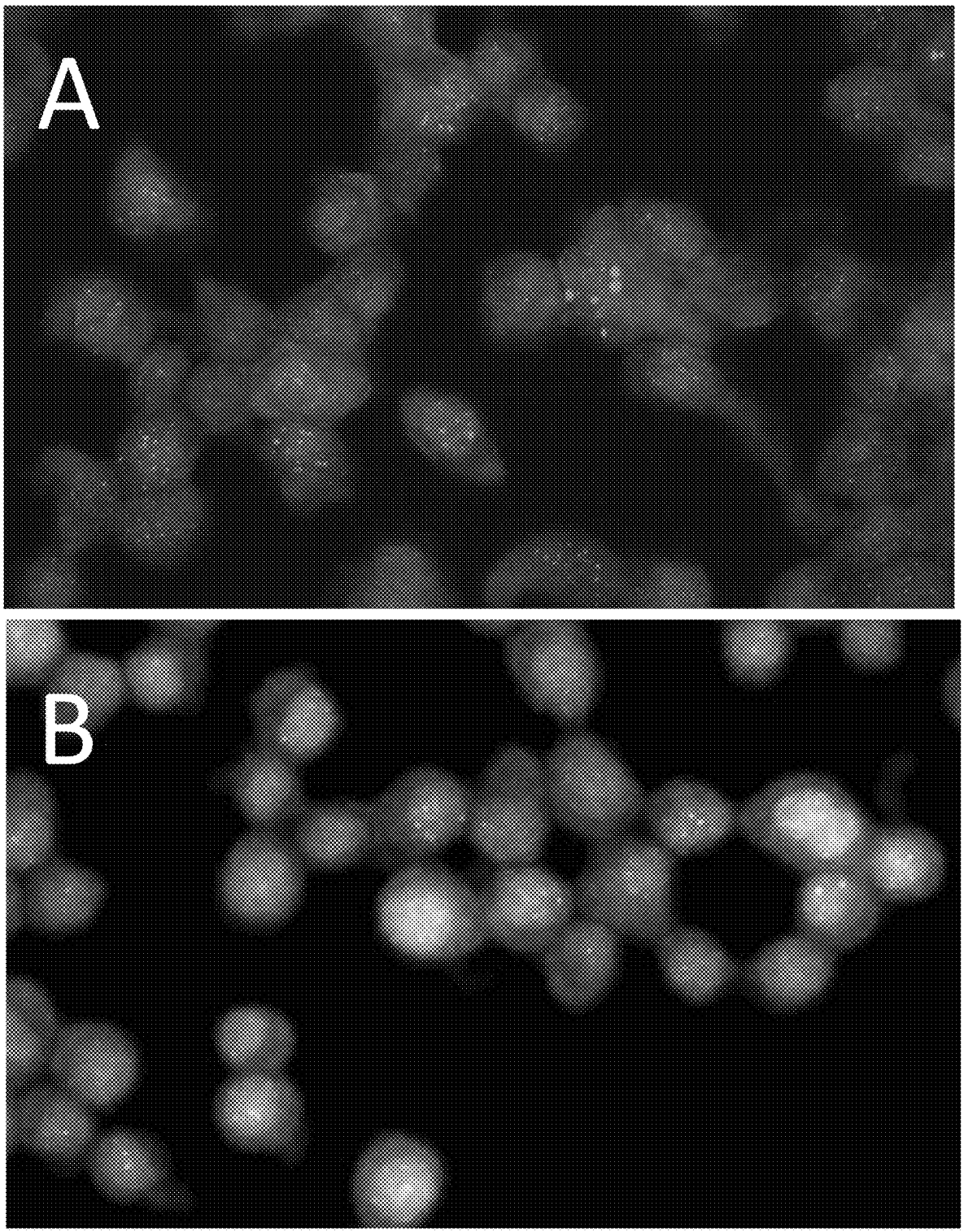
FIG. 3A-3B (S1). Telomere-FISH and immunofluorescence co-staining for ATRX protein.

Four of the 20 cases without detectable mutations in ATRX or DAXX were ALT-positive. To determine whether ATRX and DAXX expression were also normal in these tumors, serial sections of the same tumors were immunolabeled with antibodies against the ATRX and DAXX proteins. Each of the four tumors demonstrated loss of nuclear expression of either ATRX (2 cases) or DAXX (2 cases) in either the entire tumor, or confluent parts of the tumor (FIGS. 1 and 2). Of note, the nuclear expression of the corresponding wild type partner (either DAXX or ATRX, respectively) was retained in each of these four cases. Though the immunohistochemical results on tumors with ATRX or DAXX mutations were expected, they provide excellent controls for the specificities of the antibodies used for immunolabeling. Notably, each of the 16 tumors without ALT showed robust nuclear labeling for both ATRX and DAXX (Table 1). The relationship between ALT-positivity and abnormal immunolabeling for either the ATRX or DAXX proteins was statistically significant (p=0.012 and p=0.003, respectively).

In sum, there was a perfect correlation between the absence of nuclear ATRX or DAXX expression and the ALT phenotype and >80% of the 23 tumors without ATRX or DAXX expression could be accounted for by point mutations and small indels, i.e., inactivating mutations of the ATRX or DAXX genes.

Example 2

ATRX Mutations in Cancers of the CNS

To ascertain whether ATRX and DAXX gene mutations might be more generally associated with the ALT-phenotype, we examined 447 tumors of other types. We identified a low to moderate frequency of ATRX mutations in cancers of the CNS. Specifically, mutations were detected in 2 of 18 (11.1%) pediatric GBM, 8 of 123 (6.5%) adult GBM, 1 of 13 (7.7%) oligodendrogliomas, and 1 of 65 (1.5%) medulloblastomas. No mutations in either ATRX or DAXX were identified in 11 adult neuroblastomas, or in 25 ovarian adenocarcinomas, 96 breast adenocarcinomas and 96 pancreatic adenocarcinomas.

Further, ATRX mutations were found in anaplastic astrocytomas (41%), astrocytomas (29%), anaplastic oligoastrocytomas (20%), oliogoastrocytomas (33%), anaplastic oligogliomas (7%), and oligogliomas (14%). These mutations were highly associated with mutations in IDH1/2 and TP53.

Example 3

To determine if the ALT status of these additional tumor types also correlated with the presence of somatic ATRXX mutations, we performed telomere FISH as described above on 8 ATRX mutant cases in which tumor material was available. In each of the eight cases, extremely bright telomeric foci indicating ALT were identified in the neoplastic cells but not in the non-neoplastic cells surrounding them (examples in FIGS. 1 and 2) Immunolabeling with antibodies to DAXX or ATRX showed that these tumors had lost nuclear expression of ATRX. As controls, we studied 23 ATRX and DAXX-wild type tumors of the same types with the identical techniques. None of the tumors without ATRX or DAXX mutations demonstrated the ALT phenotype by telomere FISH and all 23 retained robust nuclear labeling for both ATRX and DAXX.

Example 4

ATRX Mutated in Established Cancer Cell Line

For future mechanistic studies, we considered it important to determine whether a human cancer cell line with a mutation in ATRX or DAX(could be identified. We chose to study U-2 OS, derived from an osteosarcoma, as this line was a prototype for delineating the ALT phenotype.(7) We found that exons 2 to 19 of ATRX were homozygously deleted in these cells, unequivocally inactivating the gene product, causing a lack of ATRX immunolabeling in these cells (Suppl. FIG. S1).

Example 5

Discussion

The results described above show a remarkable correlation between inactivation of ATRX or DAX(and the ALT phenotype in unrelated tumor types. Though we cannot infer from these data that mutations in ATRX or DAXX actually cause this phenotype, prior studies provide a mechanism through which this might occur. It has been proposed that ATRX-DAXX function in replication-independent heterochromatin assembly at specific repetitive G-rich regions, such as the telomeres.(16, 18, 19) In patients with the ATRX syndrome, mutations in the ATRX gene lead to changes in the DNA methylation status at subtelomeric regions which, as described below, may impact telomere stability.(30) Furthermore, experimentally decreasing ATRX or H3.3 in mouse ES cells results in telomere destabilization and an up-regulation of telomere repeat-containing RNA (TERRA).(19-21, 31)

Current evidence indicates that the ALT telomere maintenance mechanism is dependent upon homologous recombination (HR).(8, 32) Telomeres are composed of long tracts of highly repetitive DNA terminating in single stranded 3' ends, which should provide an ideal substrate for HR; thus, it has been proposed that HR at telomeres is actively suppressed in normal cells.(29) In agreement with this, somatic cell telomeric and proximal subtelomeric DNA feature tightly packed nucleosomes organized in a repressive heterochromatic state enriched for repressive epigenetic chromatin marks, such as DNA methylation and trimethylation of lysine 9 on histone H3 and of lysine 20 on histone H4.(22-24, 33) Mice engineered to contain reduced levels of such repressive epigenetic marks possess abnormally long and heterogeneous telomeres, as well as increased levels of inter-chromatid telomere recombination—all of which are hallmarks of the ALT phenotype.(22, 23) Our results are consistent with a model in which loss of ATRX-DAXX function impairs the heterochromatic state of the telomeres, perhaps due to reduced levels of H3.3 incorporation, leading to telomere destabilization and increased HR at the telomeres; thus, facilitating the development of ALT.

Example 6

Methods

Tissue Samples and Mutational Analysis

In order to assess the potential consequences of ATRX and DAXX gene mutations on telomeres, 41 sporadic, nonfunctional PanNETs were chosen from a series of PanNETs whose ATRX and DAXX gene mutational status was previously determined by exomic sequencing.(1) Of the 41 PanNETs examined, ten had ATRX gene mutations, eleven had DAXX gene mutations, and the remaining 20 had wild type ATRX and DAXX genes. Details on the specific gene mutations as well as clinicopathologic variables for this PanNET series are presented in Supplementary Table S2. Clinical information on the patients evaluated in this study was obtained from the Johns Hopkins Hospital in the context of approved IRB protocols. The ATRX and DAXX genes were also sequenced in 65 cases of medulloblastoma, 13 cases of oligodendroglioma, 141 cases of glioblastoma multiforma (18 pediatric GBM and 123 adult GBM), 11 neuroblastomas, 25 ovarian carcinomas, 96 breast carcinomas and 96 pancreatic ductal adenocarcinomas.

Immunohistochemistry

Immunolabeling for the ATRX and DAXX proteins was performed on formalin-fixed, paraffin embedded sections as previously described.(1) Briefly, heat-induced antigen retrieval was performed in a steamer using citrate buffer (catalog #H-3300, Vector Laboratories) for 30 minutes. Endogenous peroxidase was blocked (catalog #52003, Dako) and serial sections were then incubated with primary antibody; anti-ATRX (1:400 dilution; catalog #HPA001906, Sigma-Aldrich, lot R00473) or anti-DAXX (1:150 dilution; catalog #HPA008736, Sigma-Aldrich, lot A39105) for 1 hour at room temperature. The primary antibodies were detected by 30 minute incubation with HRP-labeled secondary antibody (catalog #PV6119, Leica Microsystems) followed by detection with 3,3'-Diaminobenzidine (Sigma-Aldrich), counterstaining with Harris hematoxylin, rehydration and mounting. Only nuclear labeling of either protein was evaluated. The immunolabeled PanNET slides were assessed and scored by 2 authors (R. H. and A. M.); the immunolabeled CNS tumor slides were assessed by F.R. Internal controls included islets of Langerhans in PanNETs and endothelial cells (including within intra-tumoral vessels) which demonstrated strong nuclear immunolabeling for both ATRX and DAXX.

Telomere-specific FISH and Microscopy

Combined telomere-specific FISH and immunofluorescence labeling for ATRX, DAXX and PML was conducted as previously described.(2, 3) Briefly, deparaffinized slides were hydrated, steamed for 20 minutes in citrate buffer (catalog #H-3300; Vector Laboratories), dehydrated and hybridized with a Cy3-labeled peptide nucleic acid (PNA) probe complementary to the mammalian telomere repeat sequence ([N-terminus to C-terminus] CCCTAACCCTAACCCTAA; SEQ ID NO: 1). As a positive control for hybridization efficiency, a FITC-labeled PNA probe having specificity for human centromeric DNA repeats (ATTCGTTGGAAACGGGA (SEQ ID NO: 2); CENP-B binding sequence) was also included in the hybridization solution.(4) Following post-hybridization washes, the desired primary antibody was applied (anti-ATRX, as described above; anti-DAXX, as described above; anti-PML antibody, 45 minute incubation at 1:100 dilution; catalog #PG-M3, DAKO), followed by application of species-appropriate Alexa 488 fluorescent secondary antibody (Molecular Probes Cat.#A-11034 and A-11001) and nuclear counterstaining with DAPI. Slides were imaged with a Nikon 50i epifluorescence microscope equipped with X-Cite series 120 illuminator (EXFO Photonics Solutions Inc., Ontario, Calif.) and appropriate fluorescence excitation/emission filters. Grayscale images were captured for using Nikon NIS-Elements software and an attached Photometrics CoolsnapEZ digital camera, pseudo-colored and merged. Quantification from the digital images was conducted using Telometer, a custom software plugin created for the open source image analysis program ImageJ, freely available for download (protocol http, domain bui2.win.ad.jhu, top level domain name edu, filename telometer/)

The FISH and immunolabeled slides were assessed and scored independently by 2 authors (C. H. and A. K. M.). The gold standard for determining the presence of ALT is the demonstration of telomere length maintenance over time in a continually growing cell population lacking any evidence of telomerase activity.(5) This standard, however, cannot be applied to fixed clinical specimens. Previously, it was shown that subsets of cells in ALT-positive cell lines harbor unusually large promyelocytic leukemia (PML) nuclear bodies which contain large amounts of telomeric DNA (ALT-associated PML bodies; APBs).(6) APBs are not observed in normal cells, nor are they observed in ALT-negative cancer cells, and thus APBs serve as specific biomarkers of ALT. APBs can be readily visualized in fixed tissues by combining telomere-specific FISH with fluorescent immunostaining for PML protein.(3) This method has been extensively validated and allows for the straightforward identification of ALT-positive cancers in fixed human tissue specimens.(7) APB-associated telomeric DNA aggregates are unique to ALT-positive cell populations and are significantly larger and brighter than the FISH signals emanating from individual telomeres in the same cell population.

In our study, PanNETs were classified as ALT-positive if they met the following criteria: (1) the presence of ultra-bright, intra-nuclear foci of telomere FISH signals, with integrated total signal intensities for individual foci being >10 fold that of the per cell mean integrated signal intensities for all telomeric signals in individual benign stromal cells within the same case; (2) ≥1% of neoplastic cells displaying ALT-associated telomeric DNA foci. Tumor samples lacking ALT-associated telomeric foci in which at least 5000 cells were assessed were considered ALT-negative. In all cases, areas exhibiting necrosis were excluded from consideration.

REFERENCES FOR EXAMPLE 6 ONLY

The contents of each are expressly incorporated herein.
1. Y. Jiao et al., *Science* (January 20).
2. A. K. Meeker et al., *Am J Pathol* 160, 1259 (April 2002).
3. E. Montgomery, P. Argani, J. L. Hicks, A. M. DeMarzo, A. K. Meeker, *Am J Pathol* 164, 1523 (May 2004).
4. C. Chen, Y. K. Hong, S. D. Ontiveros, M. Egholm, W. M. Strauss, *Mamm Genome* 10, 13 (January 1999).
5. J. D. Henson, R. R. Reddel, *FEBS Lett* 584, 3800 (September 10).
6. T. R. Yeager et al., *Cancer Res* 59, 4175 (Sep. 1, 1999).
7. J. D. Henson et al., *Clin Cancer Res* 11, 217 (Jan. 1, 2005).

REFERENCES (FOR ALL BUT EXAMPLE 6)

The disclosure of each reference cited is expressly incorporated herein.
1. E. H. Blackburn, *Nature* 350, 569 (Apr. 18, 1991).
2. M. Z. Levy, R. C. Allsopp, A. B. Futcher, C. W. Greider, C. B. Harley, *J Mol Biol* 225, 951 (Jun. 20, 1992).
3. A. M. Olovnikov, *J Theor Biol* 41, 181 (Sep. 14, 1973).
4. J. W. Shay, S. Bacchetti, *Eur J Cancer* 33, 787 (April 1997).
5. A. K. Meeker, D. S. Coffey, *Biochemistry* (Mosc) 62, 1323 (November 1997).
6. R. R. Reddel, T. M. Bryan, L. M. Colgin, K. T. Perrem, T. R. Yeager, *Radiat Res* 155, 194 (January 2001).
7. T. M. Bryan, A. Englezou, L. Dalla-Pozza, M. A. Dunham, R. R. Reddel, *Nat Med* 3, 1271 (November 1997).
8. J. D. Henson, R. R. Reddel, *FEBS Lett* 584, 3800 (September 10).
9. C. M. H. A. P. Subhawong, S M Hong, M. Goggins, E. A. Montgomery, E. Gabrielson, G. J. Netto, W. H. Westra, P. Argani, C. A. Iacobuzio-Donahue, I M Shih, M. Torbenson, and A. K. Meeker, in 100*th Annual Meeting of the United States and Canadian Academy of Pathology.* (Nature Publishing Group, Modern Pathology, Volume 24, Supplement 1, February 2011, San Antonio, Tex. U.S.A., 2011).
10. Y. Jiao et al., *Science* (January 20).
11. Y. Xue et al., *Proc Natl Acad Sci USA* 100, 10635 (Sep. 16, 2003).
12. R. J. Gibbons, D. J. Picketts, L. Villard, D. R. Higgs, *Cell* 80, 837 (Mar. 24, 1995).
13. R. Gibbons, *Orphanet J Rare Dis* 1, 15 (2006).
14. R. J. Gibbons et al., *Hum Mutat* 29, 796 (June 2008).
15. H. M. Shih, C. C. Chang, H. Y. Kuo, D. Y. Lin, *Biochem Soc Trans* 35, 1397 (December 2007).
16. S. J. Elsaesser, C. D. Allis, *Cold Spring Harb Symp Quant Biol* (December 7).
17. P. W. Lewis, S. J. Elsaesser, K. M. Noh, S. C. Stadler, C. D. Allis, *Proc Natl Acad Sci USA* 107, 14075 (August 10).
18. M. J. Law et al., *Cell* 143, 367 (October 29).
19. A. D. Goldberg et al., *Cell* 140, 678 (March 5).
20. L. H. Wong et al., *Genome Res* 20, 351 (March).
21. L. H. Wong et al., *Genome Res* 19, 404 (March 2009).
22. M. Garcia-Cao, R. O'Sullivan, A. H. Peters, T. Jenuwein, M. A. Blasco, *Nat Genet* 36, 94 (January 2004).
23. S. Gonzalo et al., *Nat Cell Biol* 8, 416 (April 2006).
24. G. Grafi et al., *Dev Biol* 306, 838 (Jun. 15, 2007).
25. T. R. Yeager et al., *Cancer Res* 59, 4175 (Sep. 1, 1999).
26. M. A. Cerone, C. Autexier, J. A. Londono-Vallejo, S. Bacchetti, *Oncogene* 24, 7893 (Nov. 24, 2005).
27. C. L. Fasching, K. Bower, R. R. Reddel, *Cancer Res* 65, 2722 (Apr. 1, 2005).
28. R. A. Marciniak et al., *Cancer Res* 65, 2730 (Apr. 1, 2005).
29. A. J. Cesare, R. R. Reddel, *Nat Rev Genet* 11, 319 (May).
30. R. J. Gibbons et al., *Nat Genet* 24, 368 (April 2000).
31. C. M. Azzalin, P. Reichenbach, L. Khoriauli, E. Giulotto, J. Lingner, *Science* 318, 798 (Nov. 2, 2007).
32. A. Muntoni, A. A. Neumann, M. Hills, R. R. Reddel, *Hum Mol Genet* 18, 1017 (Mar. 15, 2009).
33. V. L. Makarov, S. Lejnine, J. Bedoyan, J. P. Langmore, *Cell* 73, 775 (May 21, 1993).

The invention claimed is:

1. A method of identifying and treating a CNS tumor in a subject in need thereof, comprising:
testing for and identifying in the subject the presence of an inactivating mutation in ATRX in a tissue suspected of being a CNS tumor, or in cells or nucleic acids shed from the tumor, wherein the presence of an inactivating mutation indicates a CNS tumor, wherein the inactivating mutation is g.chrX:76778161_76778162insA, g.chrX:76824745_76824748delTCTC, g.chrX:76741670_76741673delCTAT, g.chrX:76798738_76798741delACTA, g.chrX:76825188_76825194delTTGAGGA, g.chrX:76831065delG(hom), g.chrX:76806828_76806829insT, g.chrX:76825743_76825744delTG, or g.chrX:76798774_76798775delAG(hom), and
administering to the subject an ARTX inhibitory agent or inhibitory RNA selected from the group consisting of: an antibody, an antibody fragment, a single chain antibody construct, an antisense oligonucleotide, an antisense expression construct, a siRNA, a RNA that mediates RNAi, and combinations thereof.

2. The method of claim 1, wherein the CNS tumor is a glial tumor.

3. The method of claim 1, wherein the CNS tumor is selected from the group consisting of: pediatric glioblastoma, adult glioblastoma, oligodendroglioma, medulloblastoma, anaplastic oligodendroglioma, oligoastrocytoma, anaplastic oligoastrocytoma, astrocytoma, and anaplastic astrocytoma.

4. The method of claim 1, wherein the mutation is a frameshift mutation.

5. The method of claim 2, wherein the mutation is an indel mutation.

6. The method of claim 1, wherein the step of testing for and identifying in the subject the presence of an inactivating mutation in ATRX comprises testing for and identifying the inactivating mutation in ATRX in nucleic acids shed from the tumor.

7. The method of claim 6, wherein the nucleic acids shed from the tumor is tested for an identified in one or more of: CNS fluid, blood, urine, saliva, tears, or sputum.

* * * * *

SEQUENCE LISTING

<160> NUMBER OF SEQ ID NOS: 2

<210> SEQ ID NO 1
<211> LENGTH: 18
<212> TYPE: DNA
<213> ORGANISM: Homo sapiens

<400> SEQUENCE: 1
ccctaaccct aaccctaa                                                 18

<210> SEQ ID NO 2
<211> LENGTH: 17
<212> TYPE: DNA
<213> ORGANISM: Homo sapiens

<400> SEQUENCE: 2
attcgttgga aacggga                                                  17